(12) United States Patent
Raines

(10) Patent No.: US 7,384,624 B2
(45) Date of Patent: Jun. 10, 2008

(54) ORAL CONTRAST AND METHOD OF PRODUCING THE ORAL CONTRAST

(76) Inventor: James Raines, 10180 NW. 21st Ct., Pembroke Pines, FL (US) 33026

( * ) Notice: Subject to any disclaimer, the term of this patent is extended or adjusted under 35 U.S.C. 154(b) by 335 days.

(21) Appl. No.: 11/023,070

(22) Filed: Dec. 27, 2004

(65) Prior Publication Data

US 2006/0140864 A1      Jun. 29, 2006

(51) Int. Cl.
*A61B 10/00* (2006.01)
*A61K 5/00* (2006.01)
*A61K 8/00* (2006.01)

(52) U.S. Cl. ............... 424/9.7; 424/1.11; 424/1.65; 424/9.1; 424/9.6; 424/9.4

(58) Field of Classification Search ............ 424/1.11, 424/1.37, 1.65, 9.1, 9.4, 9.5, 9.6, 9.7, 9.8, 424/400, 439; 106/35
See application file for complete search history.

(56) References Cited

U.S. PATENT DOCUMENTS 4,927,624 A    5/1990   Bryant et al.
5,242,683 A *  9/1993   Klaveness ............... 424/9.35
5,277,896 A    1/1994   Balkus, Jr.
5,352,434 A    10/1994  Illig et al.
5,385,721 A    1/1995   Baker et al.

OTHER PUBLICATIONS

Morris et al (Acta Radiologica: Diagnosis, 1985, vol. 26, No. 6, pp. 771-775).*

* cited by examiner

*Primary Examiner*—Dameron L. Jones
(74) *Attorney, Agent, or Firm*—Laurence A. Greenberg; Werner H. Stemer; Ralph E. Locher

(57) ABSTRACT

Oral contrast compositions are used as an aid for CAT scans and are ideally fast-flowing and good tasting for assisting in quick preparation of a patient in today's extremely active and busy emergency rooms. An oral contrast used for CAT scans of the esophagus, stomach, duodenum, jejunum, small intestines, colon and rectum is formed from water, diatrizoate meglumine, diatrizoate sodium, preservatives and flavorings.

20 Claims, No Drawings

ORAL CONTRAST AND METHOD OF PRODUCING THE ORAL CONTRAST

BACKGROUND OF THE INVENTION

Field of the Invention

The invention relates, generally, to an oral contrast, and to a method of making the oral contrast.

The availability of sophisticated methods such as magnetic resonant imaging (MRI) and CAT scans have contributed to the increased use of imaging technology in therapy and diagnostic studies. CAT scans are diagnostic X-ray scans or radiological scans in which cross-sectional images of a part of the body are formed through computerized axial tomography and are shown on a computer screen. Gastrointestinal tract imaging is a particular area of interest because currently used imaging agents generally provide poor imaging, resulting in visualization of little more than gross blockages or anatomical abnormalities.

There are many different types of oral contrast products in use today. Most of the oral contrasts use barium sulfate as its active ingredient. Barium sulfate is a white, thick, chalky tasting substance. Notwithstanding its relatively good contrast characteristics, barium sulfate has certain disadvantages.

Barium sulfate has a nauseating, chalky taste that makes it difficult for patients with stomach aliments to keep it down. A large number of patients having CAT scans of their abdomen and pelvis are undergoing chemotherapy and or radiation therapy. This is important because those patients are already nauseous from their other related treatments.

The hazards related with contraindications are reasons not to give barium sulfate to a patient. For example, if a patient comes to an emergency room with a ruptured appendix or diverticulum the barium sulfate could leak out into the patient's peritoneum and that can be fatal. This also holds true for any patient who is post-operative or that has esophageal, stomach, or colon cancer. Each of these patients runs the risk of the barium sulfate leaking into their peritoneum and this can result in significant complications.

The retention of barium sulfate is another problem because it can clog up a gastrointestinal tract of a patient if he/she is dehydrated. This is common in infants, the elderly and those experiencing stomach viruses.

The use of barium sulfate can cause complications in patients known to have obstruction in the colon; patients with gastrointestinal tract perforations; patients with obstructing lesions of the small intestines; patients who have pyloric stenosis which is common in infants; patients with inflammation or neoplastic lesions in the rectum; and patients who have had recent rectal biopsy.

Barium sulfate has also been known to cause bowel obstruction in pediatric patients with cystic fibrosis, and is not recommended for use with infants who have Hirshsprung Disease nor should barium sulfate be used in neonates of patients that have intussusception, ileus or blind bowel loops.

SUMMARY OF THE INVENTION

It is accordingly an object of the invention to provide an oral contrast and a method of producing the oral contrast which overcome the herein-mentioned disadvantages of the heretofore-known contrasts and methods of this general type which is fast-flowing, good tasting and is used as an aid for CAT scans of the esophagus, stomach, duodenum, jejunum, small intestines, colon and rectum.

With the foregoing and other objects in view there is provided, in accordance with the invention, a contrast composition. The contrast composition contains water, diatrizoate meglumine, diatrizoate sodium, preservatives and flavorings. The diatrizoate meglumine and diatrizoate sodium are the active ingredients.

Other characteristic features of the invention are set forth in the appended claims.

Although the invention is illustrated and described herein as embodied in an oral contrast and a method of producing the oral contrast, it is nevertheless not intended to be limited to the details explained, since various modifications and structural changes may be made therein without departing from the spirit of the invention and within the scope and range of equivalents of the claims.

The construction of the invention, however, together with additional objects and advantages thereof will be best understood from the following description of specific embodiments.

DESCRIPTION OF THE PREFERRED EMBODIMENT

The oral contrast according to the invention goes by the trademark name of TASTISCAN. TASTISCAN is made from the following formulation:

25-80 grams of sodium benzoate, ideally 42 grams;
25-59 grams of potassium sorbate, ideally 42 grams;
11-31 grams of salt, ideally 21 grams;
4-6 grams of sodium citrate, ideally 5 grams;
12-60 grams of cellulose gum, ideally 27 grams;
100-300 grams of BHA; ideally 165 grams;
100-300 grams of artificial flavoring, ideally 165 grams;
30-50 grams of Red Dye #40, ideally 38 grams;
100-300 grams of aspertame, ideally 200 grams;
100-300 grams of ascorbic acid, ideally 165 grams;
700-1500 grams of citric acid, ideally 1100 grams;
150-350 grams of diatrizoate meglumine, ideally 250 grams;
30-50 grams of diatrizoate sodium, ideally 38 grams;
1-3 grams of sodium, ideally 1.8 grams;
70-210 grams of iodine, ideally 139 grams; and
50-150 gallons of purified water, ideally 100 gallons.

TASTSCAN is fast flowing, and therefore the amount of time that it takes to prep a patient for a CAT scan will be significantly reduced compared to other oral contrasts. Time is critical in our overcrowded and very busy emergency rooms. The sooner a patient is prepped, the sooner a medical profession can diagnose their problem and decrease the amount of time patients spend in the emergency room. This is crucial as the number of patients to be seen in the emergency room setting has steadily increased over the past 5 years. Barium sulfate has a higher viscosity thereby requiring longer periods of time to move through the gastrointestinal tract of a patient.

TASTISCAN has a pleasing fruit punch taste similar to Hawaiian Punch. TASTISCAN relaxes the bowel and will not harden causing obstruction. TASTISCAN has no contraindications unless a patient is allergic to iodine.

Virtually every hospital and medical center in the world that does CAT scans will benefit from TASTISCAN. With over 30 million CAT scans performed annually in the United States, there is a huge need for a better tasting oral contrast.

With the population increasing and the elderly living longer the number of CAT scans performed will increase exponentially.

The invention further relates to a method of formulating TASTISCAN. Ideally, the ingredients are mixed as now described.

First, blend a given quantity of purified water (e.g. 3-7 gallons) and all of the ingredients in a first FDA approved container except for the sodium benzoate and the potassium sorbate, making sure all ingredients are dissolved resulting in a first solution. Next, dissolve the potassium sorbate and the sodium benzoate in the remaining portion of purified water in a second container resulting in a second solution. Then combine the first and second solutions into one FDA approved container. The final product in than put in single serving 8 ounce containers for sale to hospitals and other CAT scan facilities.

I claim:

1. A method for manufacturing an oral contrast composition, which comprises the steps of:
    making a first composition by mixing a first quantity of purified water, salt, sodium citrate, cellulose gum, BHA, artificial flavoring, red dye # 40, aspertame, ascorbic acid, citric acid, diatrizoate meglumine, diatrizoate sodium, sodium and iodine;
    making a second composition by mixing a second quantity of purified water, sodium benzoate, and potassium sorbate; and
    mixing the first composition and the second composition resulting in the oral contrast composition.

2. The method according to claim 1, which further comprises:
    setting the first quantity of purified water to be 3-7 gallons of water;
    setting the salt to be 11-31 grams;
    setting the sodium citrate to be 4-6 grams;
    setting the cellulose gum to be 12-60 grams; setting the BHA to be 100-300 grams;
    setting the artificial flavoring to be 100-300 grams;
    setting the red dye # 40 to be 30-50 grams;
    setting the aspertame to be 100-300 grams;
    setting the ascorbic acid to be 100-300 grams;
    setting the citric acid to be 700-1,500 grams;
    setting the diatrizoate meglumine to be 150-350 grams;
    setting the diatrizoate sodium to be 30-50 grams;
    setting the sodium to be 1-3 grams;
    setting the iodine to be 70-120 grams;
    setting the second quantity of purified water to be 45 to 145 gallons;
    setting the sodium benzoate to be 25-80 grams; and
    setting the potassium sorbate to be 25-59 grams.

3. The method according to claim 1, which further comprises:
    setting the first quantity of water to be 5 gallons of purified water;
    setting the salt to be 21 grams;
    setting the sodium citrate to be 5 grams;
    setting the cellulose gum to be 27 grams;
    setting the BHA to be 165 grams;
    setting the artificial flavoring to be 165 grams;
    setting the red dye # 40 to be 38 grams;
    setting the aspertame to be 200 grams;
    setting the ascorbic acid to be 165 grams;
    setting the citric acid to be 1,100 grams;
    setting the diatrizoate meglumine to be 250 grams;
    setting the diatrizoate sodium to be 38 grams;
    setting the sodium to be 1.8 grams;
    setting the iodine to be 139 grams;
    setting the second quantity of purified water to be 95 gallons;
    setting the sodium benzoate to be 42 grams; and
    setting the potassium sorbate to be 42 grams.

4. A contrast composition, comprising:
    water;
    sodium benzoate;
    potassium sorbate;
    diatrizoate meglumine; and
    diatrizoate sodium.

5. A method for performing a CAT scan, which comprises the steps of:
    ingesting the contrast composition according to claim 4; and performing the CAT scan procedure.

6. The contrast composition according to claim 4, further comprising:
    a single serving container containing the contrast composition.

7. The contrast composition according to claim 4, wherein:
    a quantity of said water is 50-150 gallons;
    a quantity of said diatrizoate meglumine is 150-350 grams; and
    a quantity of said diatrizoate sodium is 30-50 grams.

8. The contrast composition according to claim 7, further comprising:
    a quantity of said sodium benzoate is 25-80 grams;
    a quantity of said potassiuni sorbate is 25-59 grams;
    salt 11-31 grams;
    sodium citrate 4-6 grams;
    cellulose gum 12-60 grams; and
    BHA 100-300 grams.

9. The contrast composition according to claim 8, further comprising artificial flavoring 100-300 grams.

10. The contrast composition according to claim 8, further comprising red dye #40 30-50 grams.

11. The contrast composition according to claim 8, further comprising aspertame 100-300 grams.

12. The contrast composition according to claim 8, further comprising ascorbic acid 100-300 grams.

13. The contrast composition according to claim 8, further comprising citric acid 700-1500 grams.

14. The contrast composition according to claim 8, further comprising sodium 1-3 grams.

15. The contrast composition according to claim 8, further comprising iodine 70-210 grams.

16. The contrast composition according to claim 4, wherein:
    a quantity of said water is 100 gallons;
    a quantity of said diatrizoate meglurnine is 250 grams; and
    a quantity of said diatrizoate sodium is 38 grams.

17. The contrast composition according to claim 4, further comprising:
    salt; and
    sodium citrate.

18. The contrast composition according to claim 4, further comprising cellulose gum.

19. The contrast composition according to claim 4, further comprising BHA.

20. A contrast composition, comprising:
    water 100 gallons;
    diatrizoate meglumine 250 grams;
    diatrizoate sodium 38 grams;
    salt 21 grams;
    sodium citrate 5 grams;

cellulose gum 27 grams;
BHA 165 grams;
artificial flavoring 165 grams;
red dye #40, 38 grams;
aspertame 200 grams;
ascorbic acid 165 grams;

citric acid 1,100 grams;
sodium 1.8 grams; and
iodine 139 grams.

* * * * *